United States Patent
Kilian

(10) Patent No.: US 6,498,173 B1
(45) Date of Patent: Dec. 24, 2002

(54) SYNERGISTIC COMBINATION COMPRISING ROFLUMILAST AND A PDE-3 INHIBITOR

(75) Inventor: Ulrich Kilian, Reichenau (DE)

(73) Assignee: Altana Pharma AG, Constance (DE)

(*) Notice: Subject to any disclaimer, the term of this patent is extended or adjusted under 35 U.S.C. 154(b) by 0 days.

(21) Appl. No.: 09/959,599

(22) PCT Filed: Apr. 27, 2000

(86) PCT No.: PCT/EP00/03838

§ 371 (c)(1),
(2), (4) Date: Dec. 13, 2001

(87) PCT Pub. No.: WO00/66123

PCT Pub. Date: Nov. 9, 2000

(30) Foreign Application Priority Data

May 4, 1999 (EP) .............................. 99108808

(51) Int. Cl.$^7$ .................... A61K 31/44; A61K 31/4166; A61K 31/501
(52) U.S. Cl. .................. 514/352; 514/252.06; 514/334; 514/398
(58) Field of Search ........................ 514/252.06, 334, 514/352, 398

(56) References Cited

U.S. PATENT DOCUMENTS 5,223,504 A    6/1993  Noverola et al. ........... 514/263
5,712,298 A    1/1998  Amschler .................... 514/352
5,874,437 A *  2/1999  Garvey et al. ............... 514/258

OTHER PUBLICATIONS

Johnson–Mills et al., *Biochemical Pharmacology*, vol. 56, pp. 1065–1073, 1998.
Germain et al., *Eur Respir J.*, : 12 (6) : pp. 1334–1339, 1998.
Banner et al., British Journal of Pharmacology, 116: pp. 3169–3175, 1995.
Chem. Abstr. 128: 176402 (Apr. 13, 1998).
Hatzelmann et al., *Phosphodiesterase Inhibitors*, Academic Press, pp. 147–160, 1996.
Killian et al; The European Respiratory Journal, vol. 9, Supplement 23, Sep. 1996, P0253 "Distinct Pharmacological Effects of PDE3, PDE4, or PDE3 + PDE4 inhibition in guinea pigs".
Underwood et al., JPET 270; pp. 250–259, 1994; "Comparison of Phosphodiesterase III, IV, and dual III/IV inhibitors on bronchospasm and pulmonary eosinophil influx in guinea pigs".

* cited by examiner

Primary Examiner—Phyllis G. Spivack
(74) Attorney, Agent, or Firm—Gary M. Nath; Todd L. Juneau; Joshua B. Goldberg

(57) ABSTRACT

Combinations of N-(3,5-dichloropyrid)-3-cyclopropylmethoxy-4-difluoromethoxybenzamide, its pharmacologically tolerable salts or its N-oxide, with $PDE_3$ inhibitors, and methods of use thereof, are disclosed for therapeutic purposes.

10 Claims, No Drawings

SYNERGISTIC COMBINATION COMPRISING ROFLUMILAST AND A PDE-3 INHIBITOR

FIELD OF APPLICATION OF THE INVENTION

The invention relates to the combination of N-(3,5-dichloropyrid-4-yl)-3-cyclopropylmethoxy-4-difluoromethoxybenzamide, its pharmacologically tolerable salts or its N-oxide with known active compounds from the class of PDE3 inhibitors for therapeutic purposes.

KNOWN TECHNICAL BACKGROUND

The substances used in the combination according to the invention are, on the one hand, N-(3,5-dichloropyrid-4-yl)-3-cyclopropylmethoxy4-difluoromethoxybenzamide, Its pharmacologically tolerable salts or its N-oxide [=N-(3,5-dichloro-1-oxypyrid-4-yl)3-cyclopropylmethoxy-4-difluoromethoxybenzamide], all of them PDE4 inhibitors, which are described in the international application WO 95/01338 and, on the other hand, known active compounds from the class of PDE3 inhibitors.

Cyclic adenosine monophosphate (cAMP) and cyclic guanosine monophosphate (cGMP) are ubiquitous intracellular second messengers which are involved in many biological processes which are induced by a huge variety of extracellular stimulants. The inactivation (metabolization) of cAMP and cGMP is effected by enzymes of the cyclic nucleotide phosphodiesterase (PDE) type. At least nine different families of PDE isoenzymes have meanwhile been identified (PDE1 to PDE9).

The PDE3 and PDE4 isoenzyme families caused particular interest; a definitive role in the inactivation of cAMP is ascribed to both. Inhibitors of these isoenzymes exhibit actions on the airways, on the peripheral blood pressure, on the central nervous system (e.g. increase in respiratory rates) and anti-inflammatory actions.

The effect on the airways is essentially ascribed to the inhibition of PDE3 and, to a minor extent, also to the inhibition of PDE4. The effects on the blood pressure is regarded as mediated by PDE3, while the anti-inflammatory action and the action on the central nervous system are assigned to the inhibition of PDE4.

The combined use of the PDE4 inhibitor N-(3,5-dichloropyrid-4-yl)-3-cyclopropylmethoxy4-difluoromethoxybenzamide, its pharmacologically tolerable salts or Its N-oxide with a PDE3 inhibitor in the sense according to the invention has still not been described in the prior art.

SUBJECT OF THE INVENTION

The invention relates to the combined use of N-(3,5-dichloropyrid-4-yl)-3-cyclopropylmethoxy-4-difluoromethoxybenzamide, its pharmacologically tolerable salts or its N-oxide with a PDE3 inhibitor in the treatment of disease conditions which are based on acute or chronic obstruction of vessels and/or bronchi and/or on acute or chronic inflammation.

The preparation of N-(3,5-dichloropyrid-4-yl)-3-cyclopropylmethoxy-4-difluoromethoxybenzamide, its pharmacologically tolerable salts and its N-oxide and the use of these compounds as phosphodiesterase (PDE) 4 inhibitors is described in the international application WO 95/01338.

Pharmacologically tolerable salts of N-(3,5-dichloropyrid-4-yl)-3-cyclopropylmethoxy4-difluoromethoxybenzamide which may be mentioned are, for example, water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, the acids being employed in salt preparation—depending on whether it is a mono- or polybasic acid and depending on which salt is desired—in an equimolar quantitative ratio or one differing therefrom.

PDE3 inhibitors which can be employed according to the invention and which may be mentioned by way of example are those described or claimed in the following patents and patent applications: EP 0 653 426, EP 0 294 647, EP 0 357 788, EP 0 220 044, EP 0 326 307, EP 0 207 500, EP0406958, EP 0 150 937, EP 0 075 463, EP 0 272 914, EP 0 112 987, U.S. Pat. No. 4,963,561, U.S. Pat. No. 5,141,931, WO 96/15117, DE 28 25 048, DE 27 27 481, DE 28 47 621, DE 30 44 568, DE 28 37 161 and DE 30 21 792.

The following PDE3 inhibitors are to be emphasized here: UK-1745, (-)-(R)-NSP-307, EMD-57033, WIN-62582, WIN-63291, NSP-307, NSP-306, CI-930, SKF-95654, KF-15232, MS-857, REVIZINONE, CI-LOSTAMIDE, AMIPIZONE, SIGUAZODAN, CARBAZERAN, BEMORADAN and MOTAPIZONE. MILRINONE, ENOXIMONE, and PIMOPENDAN are particularly to be emphasized.

The chemical structure for PIMOPENDAN is as follows:

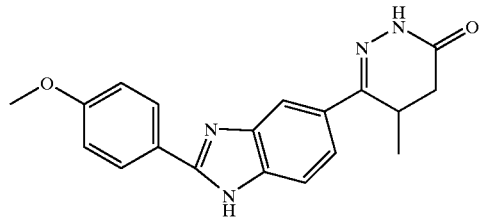

As a result of simultaneous inhibition of the two underlying metabolization routes (PDE3 and PDE4), a relative increase in the intracellular concentration of cyclic adenosine monophosphate can occur.

The biological effects of the combination following therefrom are not inevitably additive or even super-additive on cellular model systems. Surprisingly, in anesthetized, spontaneously breathing guinea-pigs treated with histamine, after administration of the combination of N-(3,5-dichloropyrid-4-yl)-3-cyclopropylmethoxy-4-difluoromethoxybenzamide with a PDE3 inhibitor a superadditive synergistic effect was observed in the inhibition of bronchospasms, while the measurements for the blood pressure and the respiratory rate remained unchanged in comparison with the individual administration of N-(3,5-dichloropyrid-4-yl)-3-cyclopropylmethoxy-4-difluoromethoxybenzamide or of a PDE3 inhibitor.

The unexpected, superadditive increase in the bronchospasmolytic activity on the combined administration of the PDE4 inhibitor N-(3,5-dichloropyrid-4-yl)-3-cyclopropylmethoxy-4-difluoromethoxybenzamide and of a PDE3 inhibitor without an influence thereby being exerted on the blood pressure or the respiratory rate, shows a particular suitability of this combination for the treatment of disease conditions such as, for example, acute, obstructive bronchitis, extrinsic or intrinsic bronchial asthma or COPD.

As a result of the combination according to the invention of N-(3,5-dichloropyrid-4-yl)-3-cyclopropylmethoxy-4-difluoromethoxybenzamide, its pharmacologically tolerable salts or its N-oxide with a PDE3 inhibitor, the individual components can be used in concentrations which on their own are not sufficiently active or not active at all. By means of this, side-effects of the individual components which would occur in the intrinsically active concentrations of N-(3,5-dichloropyrid-4-yl3cyclopropylmethoxy4-difluoromethoxybenzamide, its pharmacologically tolerable salts, its N-oxide or the PDE3 inhibitor on sole administration, are avoided by the lower concentration in the combination.

"Combined use" within the meaning of the present invention is to be understood as meaning that the individual components can be administered simultaneously in a manner which is known and customary per se [in the form of a combination medicament (as fixed or free combination)], more or less simultaneously (from one or separate pack units) or successively (directly one after the other or else also with a relatively great time interval).

In the case of more or less simultaneous administration of the individual components from separate pack units and in the case of the administration of the individual components which takes place successively, if desired a different administration form can be chosen. For example, one component can be administered by inhalation, while the other component is administered by infusion or orally.

The dose of the active compounds is of an order of magnitude customary for the dose of the individual components, it being possible, on account of the mutually positively influencing and increasing individual actions, to lower the respective doses compared with the norm on the combined administration of the active compounds. Exemplary doses for the PDE4 Inhibitor N-(3,5-dichloropyrid-4-yl)-3-cyclopropylmethoxy-4-difluoromethoxybenzamide and N-(3,5-dichloro-1-oxypyrid-4-yl)-3-cyclopropylmethoxy-4-difluoromethoxybenzamide which can be mentioned are, in the case of oral administration, a daily dose of 2 µg/kg to approximately 20 µg/kg, if appropriate in the form of a number, preferably 1 to 3, individual doses.

In the case of parenteral treatment, similar or (in particular in the case of intravenous administration of the active compound), as a rule, lower doses can be used.

The dose in the case of PDE3 inhibitors is typically in a range from 0.1 to 25 mg/kg per day.

It is known to the person skilled in the art that the optimal dose of an active compound or of an active compound combination can vary as a function of the body weight, the age and the general state of the patient, and his response behavior to the active compound or the active compound combination.

Any person skilled in the art can easily fix the optimal dose and manner of administration of the active compounds necessary in each case on the basis of his/her expert knowledge.

As medicaments, the compounds according to the invention (=active compounds) are either employed as such, or preferably are mixed with suitable pharmaceutical auxiliaries or carriers, e. g. in the form of tablets, coated tablets, capsules, emulsions, suspensions or solutions, whereby the active compounds content is advantageously between 0.1 and 95% and whereby through appropriate choice of the employed pharmaceutical auxiliaries and carriers a galenic formulation can be achieved, which is exactly adapted to the active compounds and/or the desired time of effectiveness.

The person skilled in the art is familiar with auxiliaries which are suitable for the desired pharmaceutical formulations on account of his expert knowledge. In addition to solvents, gel formers, tablet auxiliaries and other active compound excipients, for example antioxidants, dispersants, emulsifiers, preservatives, solubilizers or permeation promoters, can be used.

What is claimed is:

1. A pharmaceutical composition comprising N-(3,5-dichloropyrid-4-yl)-3-cyclopropyimethoxy-4-difluoromethoxybenzamide, its pharmacologically tolerable salts or its N-oxide in combination with a PDE3 inhibitor.

2. The combination as claimed in claim 1, wherein the PDE3 inhibitor is ENOXIMONE, MILRINONE, MILRINONE lactate or PIMOPENDAN.

3. A method of treating a disease condition which is based on acute or chronic obstruction of vessels or bronchi by administering a pharmaceutically effective amount of the compound of claim 1 to a patient in need thereof.

4. A method of treating a disease condition which is based on an acute or chronic inflammation by administering a pharmaceutically effective amount of the compound of claim 1 to a patient in need thereof.

5. A pharmaceutical composition comprising N-(3,5-dichloropyrid-4-yl)-3-cyclopropylmethoxy-4-difluoromethoxybenzamide, its pharmacologically tolerable salts or its N-oxide and a PDE3 inhibitor as a fixed or free combination together with pharmaceutically acceptable auxiliaries or excipients.

6. A pharmaceutical composition according to claim 5 wherein the active compounds a) N-(3,5-dichloropyrid-4-yl)-3-cyclopropylmethoxy-4-difluoromethoxybenzamide, its pharmacologically tolerable salts or its N-oxide and b) a PDE3 inhibitor are in a fixed combination for simultaneous administration.

7. A pharmaceutical composition according to claim 5 wherein the active compounds a) N-(3,5-dichloropyrid-4-yl)-3-cyclopropylmethoxy-4-difluoromethoxybenzamide, its pharmacologically tolerable salts or its N-oxide and b) a PDE3 inhibitor are separated from each others and packaged in one unit for simultaneous substantially simultaneous or successive administration.

8. A pharmaceutical composition according to claim 5, wherein the PDE3 inhibitor is ENOXIMONE, MILRINONE, MILRINONE lactate or PIMOPENDAN.

9. A commercial pharmaceutical product, consisting of a primary pack containing N-(3,5-dichloropyrid-4-yl)-3-cyclopropylmethoxy-4-difluoromethoxybenzamide, a pharmacologically tolerable salt or the N-oxide thereof, in combination with a secondary pack containing a PDE3 inhibitor and a package insert indicating the therapeutic treatment of disease conditions which are based on acute or chronic obstruction of vessels and/or bronchi and/or on acute or chronic inflammation.

10. A commercial pharmaceutical product, consisting of a primary pack containing a PDE3 inhibitor in combination with N-(3,5-dichloropyrid-4-yl)-3-cyclopropylmethoxy-4-difluoromethoxybenzamide, a pharmacologically tolerable salt or the N-oxide thereof, and a package insert indicating the therapeutic treatment of disease conditions which are based on acute or chronic obstruction of vessels and/or bronchi and/or on acute or chronic inflammation.

* * * * *

UNITED STATES PATENT AND TRADEMARK OFFICE
CERTIFICATE OF CORRECTION

PATENT NO.     : 6,498,173 B1  
DATED          : December 24, 2002  
INVENTOR(S)    : Ulrich Kilian Page 1 of 1

It is certified that error appears in the above-identified patent and that said Letters Patent is hereby corrected as shown below:

<u>Column 4,</u>
Line 13, please replace "dichloropyrid-4-yl)-3-cyclopropyimethoxy-4-" with
-- dichloropyrid-4-yl)-3-cyclopropylmethoxy-4- --.
Line 43, after "from each" and before "and packaged", please replace "others" with
-- other --.
Line 44, after "for simultaneous" and before "substantially simultaneous", please insert -- , --.

Signed and Sealed this

Eighth Day of April, 2003

JAMES E. ROGAN  
*Director of the United States Patent and Trademark Office*